United States Patent [19]

Desbois

[11] 4,454,350

[45] Jun. 12, 1984

[54] PROCESS FOR THE ACYLATION OF HALO- OR TRIHALOMETHYLBENZENES

[75] Inventor: Michel Desbois, Rillieux, France

[73] Assignee: Rhone-Poulenc Specialities Chimiques, Courbevoie, France

[21] Appl. No.: 392,883

[22] Filed: Jun. 28, 1982

[30] Foreign Application Priority Data

Jan. 21, 1982 [FR] France .................. 82 00877

[51] Int. Cl.$^3$ ............................................. C07C 45/46
[52] U.S. Cl. ........................... 568/319; 568/322; 568/323; 562/460; 562/461; 562/463; 562/459; 260/465 D; 564/426; 564/430; 564/442
[58] Field of Search ............... 568/319, 322, 323, 397, 568/404, 407; 562/460, 461, 463, 459; 260/465 D; 564/426, 430, 442

[56] References Cited

U.S. PATENT DOCUMENTS

| T970,006 | 5/1978 | Rose ................................ 568/322 |
| 2,273,922 | 2/1942 | Benning et al. ................ 260/649 |
| 2,275,312 | 3/1942 | Tinker et al. ................... 260/515 |
| 2,372,562 | 3/1945 | Emerson .......................... 260/592 |
| 2,735,868 | 2/1956 | Frevel et al. ................... 260/592 |
| 2,781,402 | 2/1957 | Chadwick ....................... 260/607 |
| 2,974,172 | 3/1961 | Luvisi ............................. 260/592 |
| 3,187,057 | 6/1965 | Peter et al. .................... 260/651 |
| 3,387,035 | 6/1968 | Gray et al. ..................... 260/591 |
| 3,732,307 | 5/1973 | Middleton .................. 260/566 B |
| 3,883,594 | 5/1975 | Schmaling ...................... 568/323 |
| 3,953,400 | 4/1976 | Dahl ................................ 568/322 |
| 3,967,949 | 7/1976 | Benefiel et al. .................... 71/76 |
| 4,178,460 | 12/1979 | Berkelhammer et al. ........ 562/426 |
| 4,207,266 | 6/1980 | Opie ............................ 260/651 F |
| 4,276,226 | 6/1981 | Clement et al. .............. 260/410.5 |

FOREIGN PATENT DOCUMENTS

| 43861 | 1/1982 | European Pat. Off. . |
| 876690 | 5/1953 | Fed. Rep. of Germany . |
| 1645153 | 10/1970 | Fed. Rep. of Germany . |
| 2451037 | 4/1976 | Fed. Rep. of Germany . |
| 1567806 | 4/1969 | France . |
| 2357517 | 2/1978 | France . |
| 54-135756 | 10/1979 | Japan ................................ 568/323 |
| 1164817 | 9/1969 | United Kingdom . |
| 2030158 | 4/1980 | United Kingdom . |
| 2045760 | 11/1980 | United Kingdom . |

OTHER PUBLICATIONS

Olah, Freedel-Crafts & Related Reactions III, Part II, Interscience Publn., (1964).
*Correlation Analysis in Chemistry,* Plenum Press, (ed. Chapman et al.), Table 10.1, (1978).
Morrison et al., *Organic Chemistry,* Allyn and Bacon, Inc., Boston, pp. 341–342, (3rd Edition 1973).
V. Boiko et al., Chem. Abstracts, 87:134226h, (1977).
Hansch et al., Journal of Medicinal Chemistry, vol. 16, No. 11, p. 1207, (1973).
Patai, *The Chemistry of the Carboxyl Group,* John Wiley & Sons, New York, pp. 236–237, (1966).
L. Yagupolskii, et al., Chem. Abstracts, 61:8217, (1964).
Buu-Hoi, et al., J. Org. Chem., vol. 26, pp. 2401–2402, (1961).
Fieser et al., Journal of the Amer. Chem. Soc., vol. 61, p. 1272, (1939).

Primary Examiner—James H. Reamer

[57] ABSTRACT

A process for the acylation of halo- or trihalomethylbenzenes, wherein a halo- or trihalomethylbenzene is reacted with a carboxylic acid, a precursor or a derivative thereof in the presence of boron trifluoride in an amount such that the absolute pressure of the boron trifluoride within the reaction vessel exceeds 1 bar, and in the presence of hydrofluoric acid as a solvent. The resultant products are useful as intermediates in the synthesis of compounds having a phytosanitary (e.g., herbicidal) or pharmaceutical activity.

7 Claims, No Drawings

PROCESS FOR THE ACYLATION OF HALO- OR TRIHALOMETHYLBENZENES

The instant invention is directed to a process for the acylation of halo- or trihalomethylbenzenes.

For purposes of this invention, a halo- or trihalomethylbenzene is a benzene bearing a substituent $C_nX_1(X_2)_n(X_3)_n$, wherein n equals 0 or 1 and each of $X_1$, $X_2$ and $X_3$ represents a halogen atom.

The invention is directed more particularly to the preparation of ketones by acylation, i.e., by reaction of the corresponding halo- or trihalomethylbenzene and a carboxylic acid, a precursor or a derivative thereof.

Processes for acylation are known in the art. Thus, in *Friedel-Crafts and Related Reactions* III, Part I, Interscience Publishers (1964), G. Olah describes acylation reactions in the presence of catalysts such as $AlCl_3$, $AlBr_3$, $FeCl_3$ and $SbCl_5$ in an organic solvent medium; in this process, the substrate can also be the solvent.

These processes have drawbacks which can be attributed above all to the nature of the catalyst. It is necessary to use a large quantity of catalyst. More than one mole of catalyst, such as aluminum chloride, must be used per mole of substrate, because the carbonyl group of the reagent or of the resultant ketone forms a 1:1 molar complex with aluminum chloride. The large quantity of $AlCl_3$ employed requires a correspondingly large quantity of water for its elimination. Moreover, its recovery on an industrial scale is impossible.

Acylation reactions in the presence of boron trifluoride are also known in the art (see the above-noted Olah citation). This type of reaction has only been carried out with phenols, however, which are benzenes bearing an activating substituent. The reaction has not been carried out with deactivated substrates, such as halobenzenes or trihalomethylbenzenes. Indeed, until now one skilled in the art would have believed that acylation of deactivated substrates, such as halobenzenes, could be carried out only through the use of a powerful catalytic system, such as aluminum chloride. Boron trifluoride, within the knowledge of the person skilled in the art, has been reserved exclusively for the acylation of activated derivatives, such as phenols.

It has now been discovered that $BF_3$ can be used for the acylation of deactivated substrates according to the instant invention. This is of considerable significance on an industrial scale, because the use of aluminum chloride is attended by drawbacks of a technical and economic nature not presented by boron trifluoride as used in accordance with the inventive process.

This invention is directed to a process for the acylation of halo- or trihalomethyl benzenes, characterized in that a halo- or trihalomethylbenzene is reacted with a carboxylic acid, a precursor or derivative thereof, in the presence of boron trifluoride in an amount such that the absolute pressure of the boron trifluoride inside the reaction vessel exceeds 1 bar, and in the presence of hydrofluoric acid as a solvent.

Buu-Hoi and Xuong in *J. Org. Chem.* 26, 2401–2402 (July 1961) describe the synthesis of phenolic ketones derived from di- and triphenols and from α- and β-naphthol through the condensation of carboxylic acids with the phenols in the presence of the gas generated by reaction of oleum with potassium fluoroborate. This gas contains boron trifluoride and hydrofluoric acid among other compounds, such as principally fluorosulfonic acid.

It should be noted that the reaction described in this publication takes place in a solvent medium, e.g., xylene. It should also be noted that the aromatic compound is a phenol, and therefore a benzene bearing an activating substituent (OH). This process cannot be used for the preparation of halo- or trihalomethylphenyl ketones: the solvent would react with the carboxylic acid, its precursor or derivative, because the halo- or trihalomethylbenzene is less activated than the xylene.

Moreover, the gas evolved in the reaction of oleum with potassium fluoroborate cannot be considered comparable to the boron trifluoride-hydrofluoric acid pair used in the process according to the invention. In the instant process, hydrofluoric acid in the liquid state acts as solvent, whereas in the process according to the above-noted article, it is in the gaseous state.

For purposes of this invention, the terms halobenzene and trihalomethylbenzene refer both to these compounds themselves and to their analogues with one or more substituents on the benzene nucleus.

More particularly, the invention is directed to the reaction of compounds of the formula:

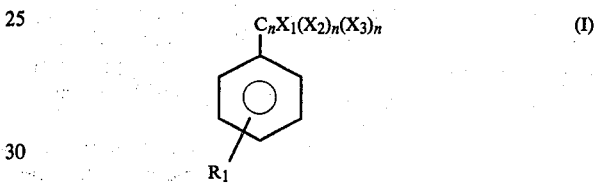

$$C_nX_1(X_2)_n(X_3)_n \quad (I)$$

wherein n is 0 or 1; $X_1$, $X_2$ and $X_3$ are identical or different and represent chlorine, bromine, iodine or fluorine; and $R_1$ represents at least one element or moiety selected from hydrogen, OH, Cl, Br, I, F, alkyl and alkoxy radicals having 1 to 6 carbon atoms and phenyl and phenoxy radicals substituted by at least one group more deactivating than the $C_nX_1(X_2)_n(X_3)_n$ group.

The phenyl and phenoxy radicals $R_1$ must be substituted by groups that are more deactivating than the group $C_nX_1(X_2)_n(X_3)_n$ so that the acylation takes place on the benzene ring bearing the $C_nX_1(X_2)_n(X_3)_n$ group. Otherwise, the acylation reaction would take place on the phenyl or phenoxy radical. Examples of groups that are more deactivating than the group $C_nX_1(X_2)_n(X_3)_n$ include $NO_2$, COOH, CN and keto groups.

When n=1, compounds of the formula I in which $X_1$, $X_2$ and $X_3$ are identical are preferred. Among the latter, those compounds in which $X_1$, $X_2$ and $X_3$ represent fluorine are particularly preferred.

The following are examples of compounds of the formula I: chlorobenzene; fluorobenzene; bromobenzene; iodobenzene; trifluoromethylbenzene; difluorobromomethylbenzene; trichloromethylbenzene; dichlorofluoromethylbenzene; tribromomethylbenzene; dibromofluoromethylbenzene; triodomethylbenzene; o-, m- and p-fluorotoluene; o-, m- and p-dichlorobenzene; o-, m- and p-fluorophenol; o-, m- and p-fluorochlorobenzene; o-, m- and p-fluoroanisole; o-, m- and p-difluorobenzene; o-, m- and p-chlorotoluene; o-, m- and p-chloroanisole; 4-trifluoromethyl-4'-chlorobiphenyl; and 4-trifluoromethyl-2,4'-dichlorodiphenyl oxide.

Within the scope of the instant invention, a carboxylic acid, a precursor or a derivative thereof would include all the conventional acylation reagents known or suggested in the art.

According to a particular embodiment of the present invention, the carboxylic acid, precursor or derivative thereof corresponds to the general formula:

$$R_2COX_4 \quad (II)$$

wherein $R_2$ represents an aliphatic or aromatic radical and $X_4$ represents halogen, a group derived from the anion of an inorganic acid, OH, $OR_3$, $OCOR_4$, $NH_2$, $NHR_5$ or $NR_6R_7$, wherein each of $R_3$, $R_4$, $R_5$, $R_6$ and $R_7$ represents an aromatic or aliphatic radical. $ClO_4^-$ and $BF_4^-$ are examples of groups derived from the anion of an inorganic acid.

Particularly well suited for use according to the invention are compounds of the Formula II in which $R_2$ represents an alkyl, phenyl, alkylphenyl or phenylalkyl radical or a phenyl radical bearing at least one substituent, such as, for example, halogen, $NO_2$, CN, $NH_2$ or COOH.

Examples of such compounds include acetyl chloride, acetic acid, acetic anhydride, benzoyl chloride, benzoic acid, benzoic anhydride, orthochlorobenzoyl chloride, parachlorobenzoyl chloride, parafluorobenzoyl chloride, paratrifluoromethylbenzoyl fluoride, orthotrifluoromethylbenzoyl fluoride, paranitrobenzoyl chloride, paranitrobenzoic acid, paraaminobenzoic acid, isobutyroyl chloride, isobutyric acid, propanoic acid, propanoyl chloride, paratoluyl chloride and parabenzylbenzoyl chloride.

The process of the invention is preferably carried out by using a quantity of hydrofluoric acid such that the molar ratio of hydrofluoric acid to the halo- or trihalomethylbenzene is between 5 and 50. Even more preferably, this ratio is between 10 and 30.

The hydrofluoric acid utilized is preferably anhydrous. The use of aqueous hydrofluoric acid would result in a useless consumption of boron trifluoride in the form of a complex of HF, $BF_3$ and $H_2O$ ($H_3O^+BF_4^-$).

The halo- or trihalomethylbenzene and the carboxylic acid, its precursor or its derivative are used in substantially equimolar quantities. A small excess of the halo- or trihalomethylbenzene may, however, be desirable.

It is particularly preferred to use a quantity of boron trifluoride such that the absolute pressure of $BF_3$ in the reaction vessel is between 6 and 20 bars. A pressure above 20 bars is not excluded from the scope of the invention but does not offer any particular advantage. The more the pressure is increased, the higher the reaction velocity. The pressure will therefore be adjusted to maximize the efficiency of the process.

The process of the invention is preferably carried out at a temperature between −20° C. and 150° C. The reaction times are generally between a few minutes and several hours.

The phenyl ketones obtained according to the process of the invention have the general formula:

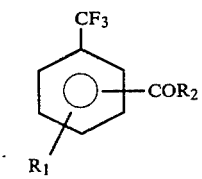

when n=1, and

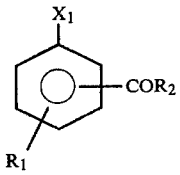

when n=0, with $X_1$, $R_1$ and $R_2$ having the same meaning as above.

The $CCl_3$, $CBr_3$, $CI_3$, $CF_2Br$, $CCl_2F$, $CBr_2F$, etc., groups are converted to $CF_3$ during the reaction in a HF medium, whereas the substituents Cl, Br and I remain unchanged.

The position of the $COR_2$ group with respect to the $CF_3$, $X_1$ and $R_1$ groups is in conformity with the substitution rules well known to the organic chemist.

The phenyl ketones obtained according to the process of the invention are useful as intermediates in the synthesis of compounds with a pharmaceutical or phytosanitary (e.g., herbicidal) activity.

The following are examples of compounds which can be prepared by the process according to the invention: 4-fluoroacetophenone; 4-chloroacetophenone; 2-fluoro-5-methylbenzophenone; 3-fluoro-6-methylbenzophenone; 2,4-dichlorobenzophenone; 2,4'-dichlorobenzophenone; 4-chloro-4'-bromobenzophenone; 4-fluoro-4'-bromobenzophenone; 4,4'-difluorobenzophenone; 4-trifluoromethyl-4'-fluorobenzophenone; 4,4'-difluoro-3-methylbenzophenone; 4,4'-difluoro-3-methoxybenzophenone; 2-fluoro-2'-chloro-5-methylbenzophenone; 3-fluoro-2'-chloro-6-methylbenzophenone; 2-fluoro-4'-chloro-5-methylbenzophenone; 3-fluoro-4'-chloro-6-methylbenzophenone; 4-fluoro-4'-chloro-3-methylbenzophenone; 2-trifluoromethyl-2'-fluoro-5-methylbenzophenone; 2-trifluoromethyl-3'-fluoro-6'-methylbenzophenone; and 4-fluoroisobutyrophenone.

In order to disclose more clearly the nature of the present invention, the following examples illustrating specific embodiments of the invention are given. It should be understood, however, that this is done solely by way of example and is intended neither to delineate the scope of the invention nor limit the ambit of the appended claims.

EXAMPLE 1

Into a 250 ml stainless steel reactor equipped with a magnetic stirring system, 100 ml of anhydrous HF, 20.8 g (0.25 mole) of acetyl chloride and 20 g (0.21 mole) of fluorobenzene were introduced at about 0° C. The reactor was closed, after which gaseous boron trifluoride ($BF_3$) was introduced until a constant pressure of 10 bars was achieved. The reaction was then allowed to proceed with stirring for 23 hours at ambient temperature. After reaction, the reactor was decompressed to atmospheric pressure, and the reaction mixture poured onto 200 g of crushed ice. The heterogeneous mixture was extracted three times with 200 ml of methylene chloride. The organic phases were washed three times with 200 ml of water, once with 200 ml of 3% aqueous potassium hydroxide solution and twice with 200 ml of water. The organic phase was dried over magnesium sulfate and the solvent eliminated by distillation under reduced pressure. 26 g (yield: 98%) of p-fluoroacetophenone (90% purity) was recovered.

EXAMPLE 2

The reaction was carried out as in Example 1 with the following compounds and under the following conditions:

| | |
|---|---|
| Anhydrous hydrofluoric acid | 100 g |
| Chlorobenzene | 22.5 g (0.2 mole) |
| Acetyl chloride | 23.6 g (0.3 mole) |
| Boron trifluoride | 6 bars at 20° C. |
| Temperature | 25° C. |
| Duration | 18 hours |

29.8 g (yield: 96.4%) of p-chloroacetophenone with 90% purity was recovered.

EXAMPLE 3

The reaction was carried out as in Example 1 with the following compounds and under the following conditions:

| | |
|---|---|
| Anhydrous hydrofluoric acid | 100 g |
| p-fluorotoluene | 22 g (0.2 mole) |
| Benzoyl chloride | 28.1 g (0.2 mole) |
| Boron trifluoride | 6 bars at 20° C. |
| Temperature | 20° C. |
| Duration | 3 hours |

37.1 g (yield: 86.7%) of a mixture of 2-fluoro-5-methylbenzophenone and 3-fluoro-6-methylbenzophenone was recovered.

EXAMPLE 4

The reaction was carried out as in Example 1 with the following compounds and under the following conditions:

| | |
|---|---|
| Anhydrous hydrofluoric acid | 100 g |
| m-dichlorobenzene | 29.4 g (0.2 mole) |
| Benzoyl chloride | 28.1 g (0.2 mole) |
| Boron trifluoride | 10 bars at 20° C. |
| Temperature | 100° C. |
| Duration | 18 hours |

44.7 g (yield: 89%) of 2,4-dichlorobenzophenone with 95% purity was recovered.

EXAMPLE 5

The reaction was carried out as in Example 1 with the following compounds and under the following conditions:

| | |
|---|---|
| Anhydrous hydrofluoric acid | 100 g |
| Chlorobenzene | 22.5 g (0.2 mole) |
| o-chlorobenzoyl chloride | 35 g (0.2 mole) |
| Boron trifluoride | 10 bars at 20° C. |
| Temperature | 20° C. |
| Duration | 23 hours |

49.1 g (yield: 97.8%) of 2,4'-dichlorobenzophenone with 97% purity was recovered.

EXAMPLE 6

The reaction was carried out as in Example 1 with the following compounds and under the following conditions:

| | |
|---|---|
| Anhydrous hydrofluoric acid | 100 g |
| Bromobenzene | 35 g (0.22 mole) |
| p-chlorobenzoyl chloride | 31.4 g (0.18 mole) |
| Boron trifluoride | 6 bars at 20° C. |
| Temperature | 20° C. |
| Duration | 2 hours |

37.4 g (yield: 70%) of 4-chloro-4'-bromobenzophenone with 95% purity was recovered.

EXAMPLE 7

The reaction was carried out as in Example 1 with the following compounds and under the following conditions:

| | |
|---|---|
| Anhydrous hydrofluoric acid | 100 g |
| Fluorobenzene | 19.2 g (0.2 mole) |
| p-fluorobenzoyl chloride | 31.7 g (0.2 mole) |
| Boron trifluoride | 10 bars at 20° C. |
| Temperature | 20° C. |
| Duration | 1 hour |

41.6 g (yield: 95.4%) of 4,4'-difluorobenzophenone with 99% purity was recovered.

EXAMPLE 8

The reaction was carried out as in Example 1 with the following compounds and under the following conditions:

| | |
|---|---|
| Anhydrous hydrofluoric acid | 100 g |
| Trifluoromethylbenzene | 29.2 g (0.2 mole) |
| p-fluorobenzoyl chloride | 31.7 g (0.2 mole) |
| Boron trifluoride | 10 bars at 20° C. |
| Temperature | 80° C. |
| Duration | 19 hours |

49.4 g (yield: 92.1%) of 4-trifluoromethyl-4'-fluorobenzophenone with 70% purity was recovered.

EXAMPLE 9

The reaction was carried out as in Example 1 with the following compounds and under the following conditions:

| | |
|---|---|
| Anhydrous hydrofluoric acid | 100 g |
| o-fluorotoluene | 22 g (0.2 mole) |
| p-fluorobenzoyl chloride | 31.7 g (0.2 mole) |
| Boron trifluoride | 10 bars at 20° C. |
| Temperature | 20° C. |
| Duration | 19 hours |

40.6 g (yield: 87.5%) of 4,4'-difluoro-3-methylbenzophenone with 97% purity was recovered.

EXAMPLE 10

The reaction was carried out as in Example 1 with the following compounds and under the following conditions:

| | |
|---|---|
| Anhydrous hydrofluoric acid | 100 g |
| o-fluoroanisole | 25.8 g (0.2 mole) |
| p-fluorobenzoyl chloride | 31.7 g (0.2 mole) |
| Boron trifluoride | 6 bars at 20° C. |
| Temperature | 10° C. |
| Duration | 1 hour |

47.8 g (yield: 96.4%) of 3,4'-difluoro-4-methoxybenzophenone with 97% purity was recovered.

EXAMPLE 11

The reaction was carried out as in Example 1 with the following compounds and under the following conditions:

| | |
|---|---|
| Anhydrous hydrofluoric acid | 100 g |
| Fluorobenzene | 19.2 g (0.2 mole) |
| Acetic anhydride | 10.2 g (0.1 mole) |
| Boron trifluoride | 10 bars at 20° C. |
| Temperature | 25° C. |
| Duration | 4 hours |

24 g (yield: 87%) of p-fluoroacetophenone with 98% purity was recovered.

EXAMPLE 12

The reaction was carried out as in Example 1 with the following compounds and under the following conditions:

| | |
|---|---|
| Anhydrous hydrofluoric acid | 100 g |
| p-fluorotoluene | 22 g (0.2 mole) |
| Benzoic anhydride | 22.6 g (0.1 mole) |
| Boron trifluoride | 10 bars at 20° C. |
| Temperature | 30° C. |
| Duration | 3 hours |

36.7 g (yield: 85.7%) of a mixture of 2-fluoro-5-methylbenzophenone and 3-fluoro-6-methylbenzophenone was recovered.

EXAMPLE 13

The reaction was carried out as in Example 1 with the following compounds and under the following conditions:

| | |
|---|---|
| Anhydrous hydrofluoric acid | 100 g |
| Fluorobenzene | 19.2 g (0.2 mole) |
| Acetic acid | 12 g (0.2 mole) |
| Boron trifluoride | 10 bars at 20° C. |
| Temperature | 50° C. |
| Duration | 5 hours |

17 g (yield: 61.5%) of p-fluoroacetophenone with 99.5% purity was recovered.

EXAMPLE 14

The reaction was carried out as in Example 1 with the following compounds and under the following conditions:

| | |
|---|---|
| Anhydrous hydrofluoric acid | 100 g |
| Fluorobenzene | 19.2 g (0.2 mole) |
| Benzoic acid | 24.4 g (0.2 mole) |
| Boron trifluoride | 15 bars at 20° C. |
| Temperature | 50° C. |
| Duration | 4½ hours |

36.3 g (yield: 90.7%) of 4-fluorobenzophenone with 99% purity was recovered.

EXAMPLE 15

The reaction was carried out as in Example 1 with the following compounds and under the following conditions:

| | |
|---|---|
| Anhydrous hydrofluoric acid | 100 g |
| p-fluorotoluene | 22 g (0.2 mole) |
| Benzoic acid | 24.4 g (0.2 mole) |
| Boron trifluoride | 10 bars at 20° C. |
| Temperature | 50° C. |
| Duration | 4 hours |

34.4 g (yield: 80.4%) of a mixture of 2-fluoro-5-methylbenzophenone and 3-fluoro-6-methylbenzophenone was recovered.

EXAMPLE 16

The reaction was carried out as in Example 1 with the following compounds and under the following conditions:

| | |
|---|---|
| Anhydrous hydrofluoric acid | 100 g |
| Fluorobenzene | 19.2 g (0.2 mole) |
| p-trifluoromethylbenzoyl fluoride | 38.4 g (0.2 mole) |
| Boron trifluoride | 6 bars at 20° C. |
| Temperature | 20° C. |
| Duration | 4 hours |

48 g (yield: 89.5%) of 4-trifluoromethyl-4'-fluorobenzophenone with 99% purity was recovered.

EXAMPLE 17

The reaction was carried out as in Example 1 with the following compounds and under the following conditions:

| | |
|---|---|
| Anhydrous hydrofluoric acid | 100 g |
| p-fluorotoluene | 22 g (0.2 mole) |
| o-trifluoromethylbenzoyl fluoride | 38.4 g (0.2 mole) |
| Boron trifluoride | 6 bars at 20° C. |
| Temperature | 23° C. |
| Duration | 1 hour |

42.6 g (yield: 75%) of a mixture of 2-trifluoromethyl-2'-fluoro-5'-methylbenzophenone and 2-trifluoromethyl-3'-fluoro-6'-methylbenzophenone was recovered.

EXAMPLE 18

The reaction was carried out as in Example 1 with the following compounds and under the following conditions:

| | |
|---|---|
| Anhydrous hydrofluoric acid | 100 g |
| 3-chloro-1-fluorobenzene | 13 g (0.1 mole) |
| p-fluorobenzoyl chloride | 15.9 g (0.1 mole) |
| Boron trifluoride | 6 bars at 20° C. |
| Temperature | 100° C. |
| Duration | 13 hours |

23.4 g (yield: 81%) of a mixture of 4,4'-difluoro-2-chlorobenzophenone and 2,4'-difluoro-4-chlorobenzophenone in a ratio of 55:45 was recovered.

EXAMPLE 19

The reaction was carried out as in Example 1 with the following compounds and under the following conditions:

| | |
|---|---|
| Anhydrous hydrofluoric acid | 100 g |
| 3-fluorophenol | 23.4 g (0.2 mole) |
| o-chlorobenzoyl chloride | 35 g (0.2 mole) |

| | |
|---|---|
| Boron trifluoride | 6 bars at 20° C. |
| Temperature | 0° C. |
| Duration | 1 hour |

48.2 g (yield: 96.2%) of a mixture of 4-fluoro-2'-chloro-2-hydroxybenzophenone and 2-fluoro-2'-chloro-4-hydroxybenzophenone was recovered. In this example, the washing with a 3% aqueous potassium hydroxide solution was eliminated in order not to extract the product phenol.

EXAMPLE 20

The reaction was carried out as in Example 1 with the following compounds and under the following conditions:

| | |
|---|---|
| Anhydrous hydrofluoric acid | 100 g |
| Trichloromethylbenzene | 39.1 g (0.2 mole) |
| p-fluorobenzoyl chloride | 31.7 g (0.2 mole) |
| Boron trifluoride | 10 bars at 20° C. |
| Temperature | 80° C. |
| Duration | 20 hours |

42 g (yield: 78%) of 4-trifluoromethyl-4'-fluorobenzophenone with 65% purity was recovered. During the reaction, an increase in pressure was noted due to the generation of hydrochloric acid resulting from the Cl-F exchange.

EXAMPLE 21

The reaction was carried out as in Example 1 with the following compounds and under the following conditions:

| | |
|---|---|
| Anhydrous hydrofluoric acid | 100 g |
| 4-fluorophenol | 23.4 g (0.2 mole) |
| Parachlorobenzoyl chloride | 35 g (0.2 mole) |
| Boron trifluoride | 6 bars at 20° C. |
| Temperature | 80° C. |
| Duration | 20 hours |

45 g (yield: 80%) of 3-fluoro-4'-chloro-2-hydroxybenzophenone with 92% purity was recovered. In this example, the washing with a 3% aqueous potassium hydroxide solution was eliminated in order not to extract the product phenol.

EXAMPLE 22

The reaction was carried out as in Example 1 with the following compounds and under the following conditions:

| | |
|---|---|
| Anhydrous hydrofluoric acid | 100 g |
| Difluorobromomethylbenzene | 41.4 g (0.2 mole) |
| p-fluorobenzoyl chloride | 31.7 g (0.2 mole) |
| Boron trifluoride | 10 bars at 20° C. |
| Temperature | 100° C. |
| Duration | 15 hours |

48 g (yield: 89%) of 4-trifluoromethyl-4'-fluorobenzophenone with 72% purity was recovered. During the reaction, an increase in pressure was noted due to the generation of hydrobromic acid resulting from the Br-F exchange.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed.

I claim:

1. A process for the preparation of phenyl ketones having the formulas:

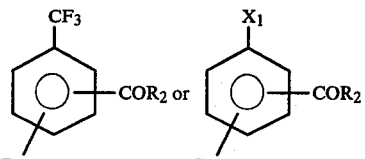

said process comprising acylation of halobenzene or trihalomethylbenzene having the formula:

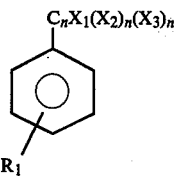

in a reaction vessel with a carboxylic acid, a derivative, or a precursor thereof having the formula:

$$R_2COX_4 \qquad (III)$$

in the presence of boron trifluoride in an amount such that the absolute pressure of the boron trifluoride within the reaction vessel exceeds 1 bar, and in the presence of hydrofluoric acid as a solvent; wherein $X_1$, $X_2$, and $X_3$ are identical or different and represent Cl, Br, I, or F;

$X_4$ represents halogen, a group derived from the anion of an inorganic acid, OH, $OR_3$, $OCOR_4$, $NH_2$, $NHR_5$, or $NR_6R_7$, wherein each of $R_3$, $R_4$, $R_5$, $R_6$, and $R_7$ is an aromatic or aliphatic radical;

n is zero or one;

$R_1$ represents at least one element or moiety selected from hydrogen, OH, Cl, Br, I, F, alkyl and alkoxy radicals having from 1 to 6 carbon atoms, and phenyl and phenoxy radicals substituted by at least one group more deactivating than the $C_nX_1(X_2)_n(X_3)_n$ group; and $R_2$ represents an aliphatic or aromatic radical.

2. A process according to claim 1 wherein $R_2$ is a radical selected from the group consisting of alkyl, phenyl, alkylphenyl, phenylalkyl, and phenyl bearing at least one halogen, $NO_2$, CN, $NH_2$, or COOH substituent.

3. A process according to claim 1 wherein an amount of hydrofluoric acid is used such that the molar ratio of the hydrofluoric acid to the compound of formula II is between 5 and 50.

4. A process according to claim 1 wherein the hydrofluoric acid used is anhydrous hydrofluoric acid.

5. A process according to claim 1 wherein the compounds of formulas II and III are used in substantially equimolar amounts.

6. A process according to claim 1 wherein an amount of boron trifluoride is used such that the absolute pressure of $BF_3$ within the reaction vessel is from 6 to 20 bars.

7. A process according to claim 1 wherein the reaction temperature is from −20° C. to 150° C.

* * * * *